(12) United States Patent
George et al.

(10) Patent No.: US 10,517,805 B2
(45) Date of Patent: Dec. 31, 2019

(54) COSMETIC COMPOSITIONS HAVING MECHANICALLY ACTIVATED WARMING ENHANCEMENT

(71) Applicant: L'Oréal, Paris (FR)

(72) Inventors: Kelly George, Paris (FR); Mickaël Poletti, Paris (FR); Allison Elder, Paris (FR); Gerald Keith Brewer, Redmond, WA (US); Aaron David Poole, Federal Way, WA (US)

( * ) Notice: Subject to any disclaimer, the term of this patent is extended or adjusted under 35 U.S.C. 154(b) by 39 days.

(21) Appl. No.: 14/986,024

(22) Filed: Dec. 31, 2015

(65) Prior Publication Data
US 2017/0189286 A1    Jul. 6, 2017

(51) Int. Cl.
*A61K 8/23* (2006.01)
*A46B 13/00* (2006.01)
*A46B 13/02* (2006.01)
*A61K 8/25* (2006.01)
*A61K 8/365* (2006.01)
*A61K 8/39* (2006.01)
*A61K 8/891* (2006.01)
*A61Q 1/14* (2006.01)
*A61Q 5/02* (2006.01)
*A61Q 19/00* (2006.01)
*A61Q 19/10* (2006.01)
*A61K 8/11* (2006.01)
*A61K 8/19* (2006.01)

(52) U.S. Cl.
CPC .............. *A61K 8/23* (2013.01); *A46B 13/008* (2013.01); *A46B 13/02* (2013.01); *A61K 8/11* (2013.01); *A61K 8/19* (2013.01); *A61K 8/25* (2013.01); *A61K 8/365* (2013.01); *A61K 8/39* (2013.01); *A61K 8/891* (2013.01); *A61Q 1/14* (2013.01); *A61Q 5/02* (2013.01); *A61Q 19/00* (2013.01); *A61Q 19/10* (2013.01); *A61K 2800/242* (2013.01); *A61K 2800/28* (2013.01); *A61K 2800/31* (2013.01); *A61K 2800/592* (2013.01); *A61K 2800/805* (2013.01); *A61K 2800/87* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 3,250,680 A | 5/1966 | Menkart et al. | |
| 3,702,302 A | 11/1972 | Wilson | |
| 4,626,550 A | 12/1986 | Hertzenberg | |
| 6,752,998 B2 | 6/2004 | Verdrel-Lahaxe et al. | |
| 7,081,211 B2* | 7/2006 | Li | A01M 1/2061 126/263.05 |
| 7,386,906 B2* | 6/2008 | Roth | A46B 13/06 15/21.1 |
| 2002/0156402 A1* | 10/2002 | Woog | A61H 23/0236 601/46 |
| 2004/0000660 A1* | 1/2004 | Li | A01M 1/04 252/183.11 |
| 2005/0169868 A1 | 8/2005 | Mohammadi et al. | |
| 2007/0027049 A1* | 2/2007 | Rigg | A61K 8/19 510/130 |
| 2008/0128426 A1 | 6/2008 | Rick et al. | |
| 2008/0305447 A1* | 12/2008 | Wheeler | A61K 8/26 432/29 |
| 2009/0270298 A1* | 10/2009 | Compain | A61K 8/368 510/136 |
| 2009/0291051 A1* | 11/2009 | Senee | A61K 8/19 424/59 |
| 2010/0111887 A1 | 5/2010 | Senee et al. | |
| 2014/0305458 A1* | 10/2014 | Brewer | A45D 34/041 132/200 |

FOREIGN PATENT DOCUMENTS

| | | | | |
|---|---|---|---|---|
| DE | 10 2004 038 771 A1 | 8/2005 | | |
| DE | 10 2009 007 521 A1 | 8/2010 | | |
| EP | 0 974 340 A2 | 1/2000 | | |
| EP | 1 186 286 A1 | 3/2002 | | |
| EP | 2111840 A1 | 10/2009 | | |
| EP | 2111843 A2 | 10/2009 | | |
| FR | 2930435 A1 * | 10/2009 | ............... | A61K 8/20 |
| FR | 2992554 A1 | 1/2014 | | |
| JP | 2005-350378 A | 12/2005 | | |
| JP | 2006-001906 A | 1/2006 | | |

(Continued)

OTHER PUBLICATIONS

Machine translation FR 2930435, printed 2016.*
(Continued)

*Primary Examiner* — David J Blanchard
*Assistant Examiner* — Alissa Prosser
(74) *Attorney, Agent, or Firm* — Christensen O'Connor Johnson Kindness PLLC

(57) ABSTRACT

The disclosed aspects and embodiments provide compositions, systems, and methods for applying a warming cosmetic composition in a manner that provides unexpected levels of temperature increase (on a per mass basis) and prevents aggregation of inorganic components of the composition. In one aspect, a composition is provided that includes an anhydrous medium and at least one exothermic heating agent, wherein the composition is configured to provide increased temperature when exposed to water sufficient to initiate an exothermic reaction and mixing energy, as compared to the composition when exposed to water in the absence of mixing energy.

16 Claims, 10 Drawing Sheets

(56) References Cited

FOREIGN PATENT DOCUMENTS

| | | | |
|---|---|---|---|
| JP | 2006-306843 A | 11/2006 |
| JP | 2007-039375 A | 2/2007 |
| JP | 2007-145798 A | 6/2007 |
| JP | 2009-067721 A | 4/2009 |
| WO | 93/08793 A1 | 5/1993 |
| WO | 00/76462 A1 | 12/2000 |
| WO | 01/12133 A2 | 2/2001 |
| WO | 01/12147 A1 | 2/2001 |
| WO | 01/64176 A1 | 9/2001 |
| WO | 02/05620 A2 | 1/2002 |
| WO | 02/060407 A1 | 8/2002 |
| WO | 02/060408 A1 | 8/2002 |
| WO | 02/068005 A1 | 9/2002 |
| WO | 2004/105709 A1 | 12/2004 |
| WO | 2004/108075 A2 | 12/2004 |
| WO | 2004105709 A1 | 12/2004 |
| WO | 2004108075 A2 | 12/2004 |
| WO | 2005/023194 A2 | 3/2005 |
| WO | 2006/109241 A1 | 10/2006 |
| WO | 2007/125489 A2 | 11/2007 |
| WO | 2008/049651 A1 | 5/2008 |
| WO | 2009/015108 A1 | 1/2009 |
| WO | 2009/130246 A1 | 10/2009 |

OTHER PUBLICATIONS

Clariant "PEG-150," Oct. 31, 2014; http://www.clariant.com/en/Solutions/Products/2013/12/09/18/29/Polyglykol-6000-P.*

Fruijtier-Pölloth "Safety assessment on polyethylene glycols (PEGs) and their derivatives as used in cosmetic products," Toxicology 214:1-38, 2005.*

SpecialChem Cetiol® 767 Technical Data Sheet, printed 2018; https://cosmetics.specialchem.com/product/i-basf-cetiol-767.*

Wikipedia "Glycerol," last edited Mar. 3, 2019.*

International Search Report and Written Opinion dated Jan. 10, 2017, issued in corresponding International Application No. PCT/US2016/059701, filed Oct. 31, 2016, 5 pages.

International Preliminary Report on Patentability dated Jul. 3, 2018, issued in corresponding International Application No. PCT/US2016/059701, filed Oct. 31, 2016, 9 pages.

Communication Pursuant to Article 94(3) EPC dated Aug. 26, 2019, issued in corresponding European Application No. 16794485.9, filed Oct. 31, 2016, 5 pages.

* cited by examiner

COSMETIC COMPOSITIONS HAVING MECHANICALLY ACTIVATED WARMING ENHANCEMENT

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a composition is provided that includes an anhydrous medium and at least one exothermic heating agent, wherein the composition is configured to provide increased temperature when exposed to water sufficient to initiate an exothermic reaction and mixing energy, as compared to the composition when exposed to water in the absence of mixing energy.

In another aspect, a kit is provided that includes:

a composition that includes an anhydrous medium and at least one exothermic heating agent, wherein the composition is configured to provide increased temperature when exposed to water sufficient to initiate an exothermic reaction and mixing energy, as compared to the composition when exposed to water in the absence of mixing energy; and a brush configured to:
  support the composition on a plurality of bristles of the brush;
  deliver water to the composition in an amount sufficient to initiate the exothermic reaction of the exothermic heating agent; and
  interface with a source of mechanical energy configured to provide sufficient movement of the brush to supply the mixing energy to the composition.

In another aspect, method of cleansing is provided, comprising applying mixing energy to a mixture of water and a composition as disclosed herein.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
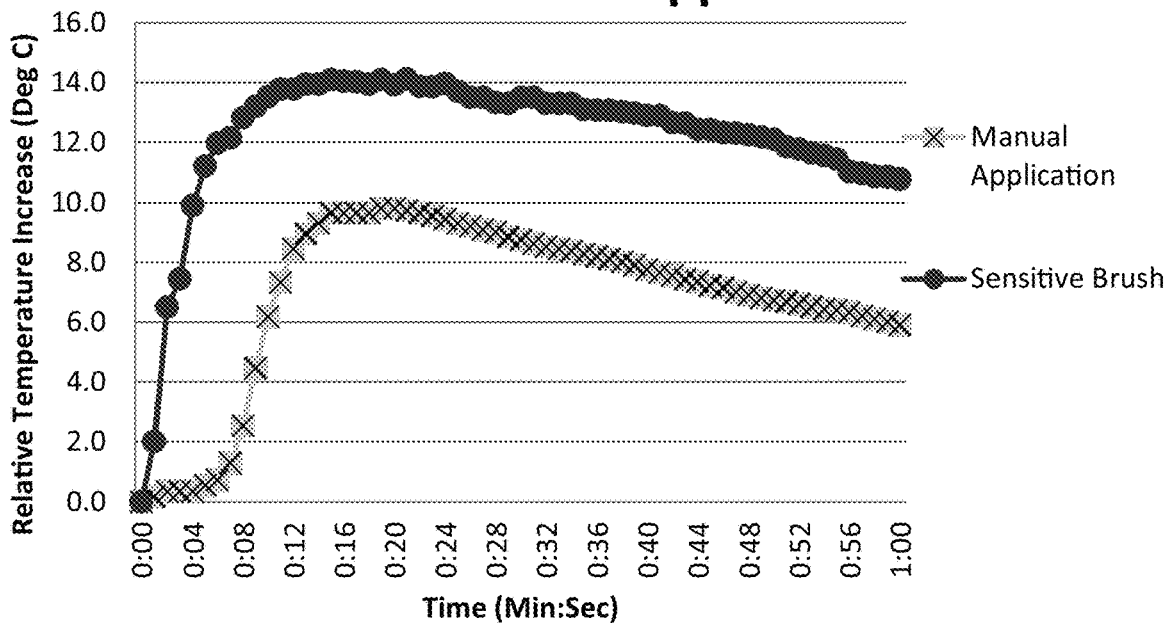
FIGS. 1-6 graphically compare temperature increase as a function of time for an exemplary composition of the present disclosure subjected to sonic energy, via an oscillating brush, or to manual application.
Figure 2:
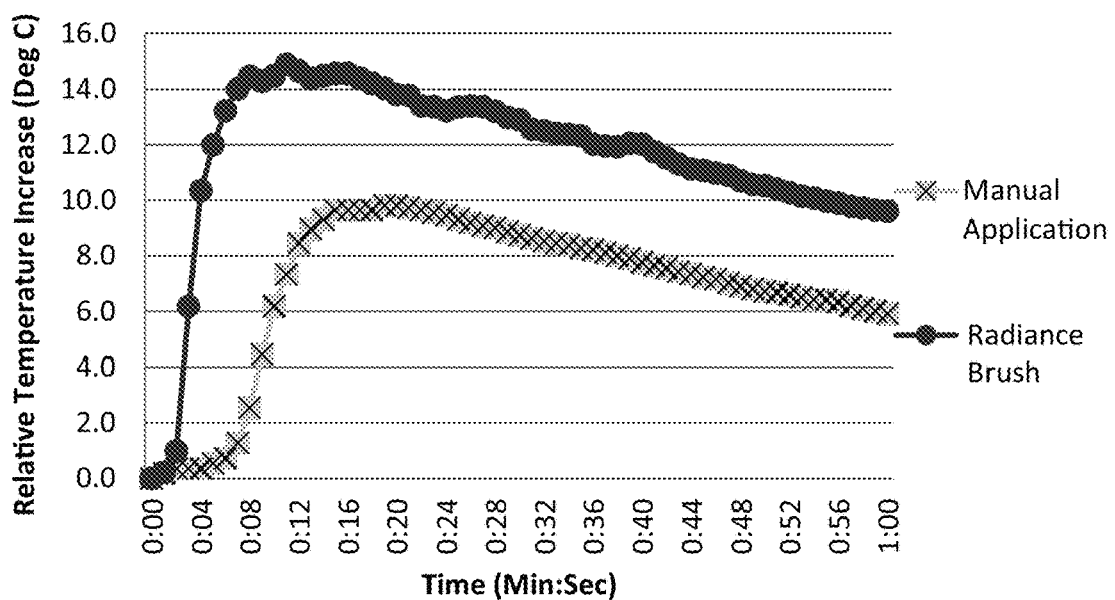

The efficacy of cosmetic products such as hair care products and skin care products are influenced by various factors, such as the amount of products applied, how long the products are applied for, the temperatures of products, and the manner of application.

A variety of approaches have been developed to obtain better efficacy from cosmetic products. For example, compositions that generate heat when mixed with water can improve penetration and deposition of conditioning components to skin and/or to hair. However, it has been found that inorganic heat-generating agents, such as inorganic salts and/or oxides, quickly agglomerate in the presence of water and form larger clumps in the presence of small amounts of water. These effects cause an uncomfortable gritty feel to the skin and/or hair, making the use of such compositions undesirable. Agglomerations may form before and/or during application of the compositions containing inorganic heat generating agents on the skin and/or hair, and may also form during storage.

While there remains a desire for obtaining enhanced efficacy from cosmetic products, such a benefit cannot come at the detriment of the user's comfort. The gritty feel of a product containing inorganic aggregates would be commercially unacceptable.

The disclosed aspects and embodiments provide compositions, systems, and methods for applying a warming cosmetic composition in a manner that provides unexpected levels of temperature increase (on a per mass basis) and prevents aggregation of inorganic components of the composition.

In one aspect, a composition is provided that includes an anhydrous medium and at least one exothermic heating agent, wherein the composition is configured to provide increased temperature when exposed to water sufficient to initiate an exothermic reaction and mixing energy, as compared to the composition when exposed to water in the absence of mixing energy. The composition (sometimes referred to herein as a "warming" or "heating" composition) produces a heating effect when exposed to water sufficient to initiate an exothermic reaction and mixing energy. The amount of water required depends on the component(s) of the composition that produce the exothermic reaction. The mixing energy, in certain embodiments, is produced by the action of a mechanical brush (e.g., a Clarisonic® brand oscillating brush), and therefore is characterized as "mechanical energy" in certain embodiments.

The mixing energy required to produce the effect is greater than can be applied manually (i.e., by hand). Therefore, the mixing energy is provided by a powered device, such as a powered brush.

In embodiments where the mixing energy is applied by a brush head, the increased heating is produced by the specific micro-environment created by the bristles of the brush head when moved at high speeds (e.g., sonic oscillation in the x-y, user's skin, plane). The micro-environment includes the brush bristles as a structure that facilitates the delivery of water to the composition, in order to generate the exothermic reaction and produce heat. Movement of the bristles generates mixing of the composition and water, reduces the potential for aggregation, disperses heat evenly from the composition, and disperses the composition evenly across the surface of the brush for application to a user.

The composition of the brush, both in terms of bristle material, bristle length, and bristle density, are all factors in how well the composition produces the exothermic effect. The primary consideration for all factors is how well the brush bristles deliver water to the composition to produce the necessary mixing. In one embodiment, the mixture of water:formula is between 1:1 and 2:1 by weight.

Insufficient water will typically yield less than optimal results. This has been demonstrated using a variety of brush designs, those holding more water, provide better heating. If too much water is supplied, the heating effect is reduced by physically flushing the slurry of water and formula off the brush face.

Sufficient mixing energy must be provided to completely and rapidly mix the formula and water. Kinetic energy from the mechanical energy source (e.g., a brush) is not sufficient to produce a temperature increase on the scale of the exothermic heating agent. For evidence of this, see FIG. 11 and the related description herein. However, higher oscillating motion of a brush does result in more effective heating, by quickly mixing both water and formula and evenly distributing it about the skin/surface.

As used herein, the term "anhydrous" refers to a composition that contains 5% or less of water, by weight, based on total weight of the composition. In one embodiment, the composition has 3% or less of water. In one embodiment, the composition has 1% or less of water.

The composition, via the exothermic heating agent, is configured to provide warming when exposed to water sufficient to initiate an exothermic reaction. As used herein, the term "exposed to water" encompasses exposure to both liquid and gaseous water. In one embodiment, the composition is exposed to liquid water, which allows for a high level of control of the reaction due to the ability to limit the amount of liquid water delivered to the composition. However, in one embodiment, the composition is exposed to gaseous water (e.g., steam or high humidity).

Exothermic Heating Agents

The exothermic heating agent (also referred to herein as the "heating agent") can be any heating agent known to produce an exothermic reaction when exposed to water. These heating agents do not include compounds that produce a warming response (e.g., via biological mechanism, such as inflammation) with human hair or human skin because such agents are not triggered by a reaction with water and do not actually produce a rise in temperature (only the sensation of heating).

In one embodiment, the exothermic heating agent is selected from polyvinyl amine; polyalkyleneamine; polyalkyleneimine; a redox system of iron powder with high surface area catalyst; silica gel; activated alumina; zeolites; kaolin; Fuller's earth; China clay; bentonite; substituted polyhydric alcohol and fatty acid ester; sulfate salts of Na, Ca, Mg, Al, Fe, Li, or K; sulfite salts of Na, Ca, Mg, Al, Fe, Li, or K; chloride salts of Na, Ca, Mg, Al, Fe, Li, or K; nitrate salts of Na, Ca, Mg, Al, Fe, Li, or K; and phosphate salts of Na, Ca, Mg, Al, Fe, Li, or K.

An exemplary polyalkyleneamine is tetrabutylenepentamine.

In one embodiment, the exothermic heating agent is iron powder, which includes elemental iron, iron oxides, and ferrous salts that can be oxidized to a ferric oxidation state, and any combinations thereof. Oxygen is delivered to the system via an aqueous phase which allows mixing with the iron powder. The combination of iron and air is activated by a catalyst. In one embodiment, the catalyst is a substance that increases surface area contact of the reactants. Activated charcoal is one embodiment of a high surface area catalyst. Other catalysts include alumina, alummosilicates, silica and a variety of clays. Although not vital to the reaction, water absorbents such as vermiculite may be utilized as an inexpensive water reservoir. Vermiculite is an aluminum-iron magnesium silicate. In certain systems, salts such as sodium chloride may be employed to further assist the reaction. Certain amounts of water can also be originally present to initiate the heating reaction. Access to air should be limited. Air (and aerated water) initiates the reaction.

In one embodiment, the composition is stored in a cosmetic product dispenser configured to seal the composition from the atmosphere during storage periods prior to use. Such storage prevents unintended initiation of the exothermic reaction due to atmospheric or unintended exposure to water.

In one embodiment, the amount of the iron powder is from about 0.1% to about 95% by weight of the composition. In one embodiment, the amount of the iron powder is from about 2% to about 50% by weight of the composition. In one embodiment, the amount of the iron powder is from about 3% to about 30% by weight of the composition. In one embodiment, the amount of the iron powder is from about 10% to about 20% by weight of the composition.

In one embodiment, the amount of the catalyst is from about 0.01% to about 30% by weight of the composition. In one embodiment, the amount of the catalyst is from about 0.1% to about 10% by weight of the composition. In one embodiment, the amount of the catalyst is from about 1% to about 5% by weight of the composition.

In one embodiment, the weight ratio of iron powder to catalyst is about 1000:1 to about 1:1000. In one embodiment, the weight ratio of iron powder to catalyst is about 100:1 to about 1:1. In one embodiment, the weight ratio of iron powder to catalyst is about 10:1 to about 2:1.

In one embodiment, vermiculite or an equivalent substance is the exothermic heating agent. In one embodiment, the amount of vermiculite is from about 0.01% to about 30% by weight of the composition. In one embodiment, the amount of vermiculite is from about 0.1% to about 10% by weight of the composition. In one embodiment, the amount of vermiculite is from about 0.5% to about 3% by weight of the composition.

In one embodiment, the exothermic heating agent is a metal salt. In one embodiment, the metal salt is selected from alkaline-earth metal salts, magnesium salts, and mixtures thereof.

As alkaline-earth metal salts, there may be mentioned in particular calcium salts and, more especially, calcium halides such as calcium iodide, chloride and bromide. In one embodiment the salt is calcium chloride.

As magnesium salts, magnesium sulfate is the salt in a particular embodiment. The Examples primarily describe magnesium sulfate as the exothermic heating agent.

In certain embodiments, a mixture of several salts is used. In one embodiment, the metal salt is selected from magnesium sulfate, calcium chloride, and mixtures thereof.

The quantity of metal salt(s), in one embodiment, is from 0.1% to 50% by weight of the composition. In another embodiment, the amount of metal salt(s) is from 5% to 40% by weight. In another embodiment, the amount of metal salt(s) is from 10% to 30% by weight.

In one embodiment, the exothermic heating agent is selected from sulfate salts of Na, Ca, Mg, Al, Fe, Li, or K; sulfite salts of Na, Ca, Mg, Al, Fe, Li, or K; chloride salts of Na, Ca, Mg, Al, Fe, Li, or K; nitrate salts of Na, Ca, Mg, Al, Fe, Li, or K; phosphate salts of Na, Ca, Mg, Al, Fe, Li, or K; and combinations thereof.

In one embodiment, the amount of metal salt(s) ranges from about 0.1% to about 50% by weight of the composition. In one embodiment, the amount of metal salt(s) ranges from about 5% to about 40% by weight of the composition. In one embodiment, the amount of metal salt(s) ranges from about 10% to about 30% by weight of the composition. The amount of the exothermic heating agent defines the amount of heating. However, the amount of the exothermic heating agent must be balanced by other considerations, such as the texture and appearance of the composition, as related to the overall user experience. Additionally, too much exothermic heating agent will physically harm the user by burning the skin. Accordingly, formulation of the compositions is not based solely on how to provide the most heating. The disclosed ranges of ingredients in the composition, including the exothermic heating agent, have been carefully considered and are optimized accordingly.

The exothermic heating agent is not, in certain embodiments, anhydrous. Therefore, for the exothermic heating agent to be incorporated into a medium that is anhydrous, a non-polar coating is used. Accordingly, in one embodiment, the exothermic heating agent is coated with an agent selected from an oil, a wax, and a surfactant.

In one embodiment, the oil, wax, or surfactant is present in the composition from 0.1% to about 90% by weight.

Surfactants

Surfactants in the composition include a single surfactant or a mixture of surfactants (often surfactant powders or in other easily used forms (liquid)). In one embodiment, the composition includes at least one ionic surfactant that includes anionic or amphoteric surfactants.

Examples of anionic surfactants include surfactants selected from these classes of surfactants: alkyl sulfates, alkyl ether sulfates, alkyl monoglyceride sulfates, alkyl monoglyceride sulfonates, alkylaryl sulfates, alkyl sulfosuccinates, alkyl ether sulfosuccinates, alkyl sulfosuccinamates, alkyl ether carboxylates, alkyla idoether carboxylates, alkyl succinates, fatty acyl taurates, fatty acyl isethionates, fatty acyl sarcosinates, fatty acyl glutamates, and alkyl phosphates. Alternative surfactants may include or be combined with foaming surfactants or foaming agents suitable for use in foaming skin cleansers or on skin cleaning fibrous pads when mixed with water. The foaming action provided surfactant use aids in exfoliation of skin cells and additional cleaning benefits allowing a crisp clean feel following wash-off by a user. While surfactant use is not required in each embodiment one optional preferred embodiment includes surfactants.

In selected embodiments, the surfactants are those having C10 to C16 in the fatty acyl part of the surfactant. In other selected embodiments, the most preferred anionic surfactants are those of isethionates, taurates, sulfosuccinates, sulfosuccinamates, and phosphates with C10 to C16 fatty acyl radical, and mixtures thereof.

Examples of amphoteric surfactants include surfactants selected from these classes of surfactants: amphocarboxylates, alkyl betaines, amidoalkyl betaines, amphophosphates, phosphobetaines, pyrophosphobetaines, carboxyalkyl polyamines, and amidoalkyl sultaines. In selected embodiments, the preferred surfactants are those having C10 to C16 in their fatty acyl part.

In alternative embodiments, the surfactant may include suitable nonionic surfactants including alkyl polyglucoside having alkyl groups from C10 to C16, and optionally cocoamidopropyl amine oxide.

The surfactant portion, based on the total weight of the surfactant portion, in certain embodiments, contains from 20% to 70% of amphoteric surfactant. In a further embodiment, the surfactant portion, based on the total weight of the surfactant portion, includes from 40% to 60% of amphoteric surfactant.

In one embodiment, the surfactant portion, based on the total weight of the surfactant portion, includes from 20% to 70% of anionic surfactant. In a further embodiment, the surfactant portion, based on the total weight of the surfactant portion, includes from 40% to 60% of anionic surfactant.

Depending upon the alternative composition, the percentage of surfactant portion, based on the total weight of the powder composition, is from 20% to 80%. In one embodiment, the percentage of surfactant portion, based on the total weight of the powder composition, is from 40% to 80%. In one embodiment, the percentage of surfactant portion, based on the total weight of the powder composition, is from 50% to 70%.

In one embodiment, the exothermic heating agent is encapsulated in a water-soluble coating. In one embodiment, the water-soluble coating comprises a PEG having a molecular weight from about 2000 to about 6000. In one embodiment, the exothermic heating agent is entirely encased by a water-soluble coating.

Anhydrous Medium

The purpose of the anhydrous medium is to support the exothermic heating agent without activating it prior to exposure to water.

In one embodiment, the anhydrous medium is an oil or combination of oils. The quantity of oil(s) in one embodiment is from about 5% to about 80% by weight of the composition. The quantity of oil(s) in one embodiment is from about 10% to about 60% by weight of the composition. The quantity of oil(s) in one embodiment is from about 10% to about 40% by weight of the composition.

The term "oil" is understood to mean a fatty substance that is liquid at room temperature (25° C.).

In one embodiment the oil is selected from vegetable and plant oils, including canola, sunflower, safflower, soybean, castor, rice bran, corn, coconut, palm, macadamia nut, almond; and synthetic oils including mineral, isoparaffin, esters, and silicone oils.

Representative oils include:

hydrocarbon oils of plant origin, such as liquid triglycerides of fatty acids comprising from 4 to 10 carbon atoms such as the triglycerides of heptanoic or octanoic acids or alternatively, for example, sweet almond oil, sunflower oil, maize oil, soybean oil, gourd oil, coriander oil, grape seed oil, sesame oil, hazelnut oil, apricot oil (*Prunus Armenica* oil), macadamia oil, arara oil, oil from rUniqeman, avocado oil, the triglycerides of caprylic/capric acids such as those sold by the company Stearineries Dubois or those sold under the names Miglyol 810, 812 and 818 by the company Dynamit Nobel, jojoba oil, shea butter oil;

synthetic esters and ethers, in particular of fatty acids, such as the oils of formulae R1COOR2 and R1OR2 in which R1 represents the residue of a fatty acid comprising from 8 to 29 carbon atoms, and R2 represents a branched or unbranched hydrocarbon chain containing from 3 to 30 carbon atoms, such as for example Purcellin oil or 660084 PCL-LIQUID from the company SYMRISE (mixture of cetylstearyl 2-ethylhexanoate and isopropyl myristate), isononyl isononanoate, isopropyl myristate, isopropyl palmitate, 2-ethylhexyl palmitate (or octyl palmitate), 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, heptanoates, octanoates and decanoates of fatty alcohols; polyol esters, such as propylene glycol dioctanoate, neopentyl glycol diheptanoate and diethylene glycol diisononanoate; and the pentaerythritol esters such as pentaerythrityl tetraisostearate;

linear or branched hydrocarbons, of mineral or synthetic origin, such as volatile or non-volatile paraffin oils, and derivatives thereof, petroleum jelly, polydecenes, hydrogenated polyisobutene such as Parleam® oil;

fatty alcohols having from 8 to 26 carbon atoms, such as cetyl alcohol, stearyl alcohol and a mixture thereof (cetearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluorinated oils such as those described in the document JP-A-2-295912. As fluorinated oils, there may also be mentioned perfluoromethylcyclopentane and perfluoro-1,3-dimethylcyclohexane, sold under the names "FLUTEC PC1®" and "FLUTEC PC3®" by the company BNFLFluorochemicals; perfluoro-1,2-dimethylcyclobutane; perfluoroalkanes such as dodecafluoropentane and tetradecafluorohexane, sold under the names "PF 5050®" and "PF 5060®" by the company 3M, or alternatively bromoperfluorooctyl sold under the name "FORALKYL®" by the company Atochem; nonafluoromethoxybutane sold under the name "MSX 4518" by the company 3M and nonafluoroethoxyisobutane; perfluoromorpholine derivatives, such as 4-trifluoromethyl-perfluoro-morpholine sold under the name "PF 5052®" by the company 3M;

silicone oils such as volatile or non-volatile polymethylsiloxanes (PDMS) containing a linear or cyclic silicone chain, which are liquid or pasty at room temperature, in particular cyclopolydimethyl-siloxanes (cyclomethicones) such as cyclohexasiloxane and cyclopentasiloxane; polydimethylsiloxanes comprising alkyl, alkoxy or phenyl groups which are pendant or at the end of the silicone chain, groups having from 2 to 24 carbon atoms; phenylated silicones such as phenyltrimethicones, phenyldimethicones, phenyltrimethylsiloxydiphenylsiloxanes, diphenyl-dimethicones, diphenylmethyldiphenyltrisiloxanes, 2-phenylethyl-trimethylsiloxysilicates, and polymethyl-phenylsiloxanes; and mixtures thereof.

The expression "hydrocarbon oil" is understood to mean, in the list of oils mentioned above, any oil predominantly containing carbon and hydrogen atoms, and optionally ester, ether, fluorinated, carboxylic acid and/or alcohol groups.

The composition can be used as a make-up removing composition, and as such, may contain one or more oils that are known to provide make-up removal benefits. The makeup-removing oils are chosen in particular from branched hydrocarbons of mineral origin, such as hydrogenated polyisobutene, the fatty acid esters described above, and mixtures thereof. Representative fatty acid esters that can be used as makeup-removing oils include ethylhexyl palmitate, ethylhexyl stearate, isopropyl myristate, isopropyl palmitate, isobutyl palmitate, pentaerythrityl caprate/caprylate, cetearyl isononanoate, isodecyl isononanoate, isononyl isononanoate, isotridecyl isononanoate, 2-ethylhexyl caprate/caprylate, and mixtures thereof.

In addition to the oils indicated above, the composition in certain embodiments includes other fatty substances, such as fatty acids containing from 8 to 30 carbon atoms, such as stearic acid; silicone resins such as trifluoromethyl-C1-4-alkyldimethicone and trifluoropropyldimethicone; silicone gums (INCI name: Dimethiconol) alone or as a mixture with a silicone oil, such as the product marketed by the company Dow Corning under the name Dow Corning 1501 Fluid, which is a mixture of Dimethiconol and Cyclopentasiloxane in the ratio 14.7/85.3 (dimethiconol); silicone elastomers such as those marketed under the names KSG by the company Shin-Etsu; waxes, for example mineral waxes, waxes of animal origin such as beeswax, waxes of plant origin, hydrogenated oils that are concrete at 25° C., fatty esters and glycerides that are concrete at 25° C., synthetic waxes such as polymethylene wax, silicone waxes; and mixtures thereof.

In certain embodiments, oil(s)s (e.g., waxes and other components including elastomers) include at least one wax of melting point in excess of 20 degrees centigrade and one oil that has a Hydrophile-Lipophile Balance (HLB) value ranging from about 1-16. Examples of waxes include, but are not limited to, natural waxes and derivatives of such waxes (derived from plants and animals) and synthetic waxes. Representative examples of waxes may also include: beeswax, carnauba wax, candelilla wax, jojoba wax, olive wax, spermaceti wax, shellac wax, montan wax, lanolin wax, polyethylene wax, microcrystalline wax, ozokerite wax, ceresin wax, petroleum and petrolatum wax and ester waxes. Further representative examples of waxes are those modified by esterification, ethoxylation, propoxylation and combinations thereof.

In one embodiment, the waxes are ethoxylated and propoxylated polyethylenes. The most preferred waxes of this optional embodiment are those having C10 to C60, propoxylation from 1 to 40 moles, and ethoxylation from 1 to 40 moles.

In one embodiment, the composition includes a thickener. Thickeners are elastomers that may be used alone as thickeners or as fillers in combination with oils, as disclosed above. Examples of suitable elastomers include, but are not limited to: Kratons (a hydrocarbon based elastomer) and EPSQ (a powdered elastomer) both available from Grant Industries, Inc. of 125 Main Avenue, Elmwood Park, N.J. 07407. Further examples of suitable thickeners include, but are not limited to, clays such as bentonites, hectorites and laponites.

Gelling Agents

In certain embodiments, the composition includes a gelling agent. In one embodiment, the gelling agent is present but is 10% or less of the total weight of the composition. In one embodiment, the gelling agent is present but is 1% or less of the total weight of the composition. In one embodiment, the gelling agent is present but is 0.5% or less of the total weight of the composition. In one embodiment, the gelling agent is present but is 0.1% or less of the total weight of the composition. In one embodiment, the composition includes no gelling agent.

The expression "gelling agent" (also called "thickening agents") is understood to mean an agent capable of modifying the viscosity of the composition. Fillers and exfoliating particles are not considered as gelling agents.

In one embodiment, the gelling agent is lipophilic or hydrophilic gelling agent selected from:

(1) Organophilic clays which are clays modified with chemical compounds which make the clay capable of swelling in oily media; by way of examples of such products, there may be mentioned clays of the smectite family such as montmorillonites, hectorites, bentonites, beidellites, saponites, and of the family comprising vermiculites, stevensite, chlorites.

These clays may be modified with a chemical compound chosen from quaternary amines, tertiary amines, amine acetates, imidazolines, amine soaps, fatty sulfates, alkyl aryl sulfonates, amine oxides, and mixtures thereof.

(2) Pyrogenic silicas which may be obtained by high-temperature hydrolysis of a volatile silicon compound in an oxyhydric flame, producing a finely divided silica. This process makes it possible in particular to obtain hydrophilic silicas which have a large number of silanol groups at their surface. Such hydrophilic silicas are for example marketed under the names "AEROSIL 130®", "AEROSIL 200®", "AEROSIL 255®", "AEROSIL 300®", "AEROSIL 380®" by the company Degussa, "CAB-β-SIL HS-5®", "CAB-O-SIL EH-5®", "CAB-O-SIL LM-130®", "CAB-O-SIL MS-55®", "CAB-O-SIL M-5®" by the company Cabot.

Silicas modified with hydrophobic groups such as trimethylsiloxyl groups, which are obtained in particular by treating pyrogenic silica in the presence of hexamethyldisilazane. Silicas thus treated are called "Silica silylate" according to the CTFA (6th edition, 1995). They are for example marketed under the references "AEROSIL R812®" by the company Degussa, "CAB-O-SIL TS-530®" by the company Cabot. Dimethylsilyloxyl or polydimethylsiloxane groups, which are in particular obtained by treating pyrogenic silica in the presence of polydimethylsiloxane or dimethyldichlorosilane. Silicas thus treated are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SM TS-720®" by the company Cabot.

(3) The homo- or copolymers of acrylic or methacrylic acids and their salts and their esters and in particular the products sold under the names "VERSICOL F" or "VERSICOL K" by the company ALLIED COLLOID, "ULTRAHOLD 8" by the company CIBA-GEIGY, polyacrylic acids of the SYNTHALEN K type, and the salts, in particular of sodium, of polyacrylic acid (corresponding to the INCI name sodium acrylate copolymer) and more particularly a crosslinked sodium polyacrylate (corresponding to the INCI name sodium acrylate copolymer (and) caprylic/capric triglyceride) sold under the name "LUVIGEL EM" by the company.

(4) The copolymers of acrylic acid and acrylamide sold in the form of their sodium salt under the names "RETEN" by the company HERCULES, sodium polymethacrylate sold under the name "DARVAN No 7" by the company VANDERBILT, the sodium salts of polyhydroxycarboxylic acids sold under the name "HYDAGEN F" by the company HENKEL (5) Polyacrylic acid/alkyl acrylate copolymers of the PEMULEN type.

(6) AMPS (polyacrylamidomethylpropanesulphonic acid partially neutralized with aqueous ammonia and highly crosslinked) marketed by the company CLARIANT.

(7) AMPS derivatives such as the AMPS/acrylamide copolymers of the SEPIGEL or SIMULGEL type marketed by the company SEPPIC, the AMPS/polyoxyethylenated alkyl methacrylate copolymers (crosslinked or not) of the ARISTOFLEX HMS type marketed by the company CLARIANT, and mixtures thereof.

(8) Proteins such as proteins of plant origin such as wheat or soybean proteins; proteins of animal origin such as keratins, for example, keratin hydrolysates and sulphonic keratins.

(9) Anionic, cationic, amphoteric or nonionic chitin or chitosan polymers.

(10) Cellulose polymers and their derivatives such as hydroxyethylcellulose, hydroxypropylcellulose, methyl-cellulose, ethylhydroxyethylcellulose, carboxymethyl-cellulose, and the quaternized derivatives of cellulose.

(11) Vinyl polymers, such as polyvinylpyrrolidones, copolymers of methyl vinyl ether and malic anhydride, copolymer of vinyl acetate and crotonic acid, copolymers of vinylpyrrolidone and vinyl acetate; copolymers of vinylpyrrolidone and caprolactam; polyvinyl alcohol.

(12) Polymers of natural origin, optionally modified, such as: gum arabic, guar gum, xanthan derivatives, karaya gum; alginates and carrageenans; glycoaminoglycans, hyaluronic acid and its derivatives; shellac resin, sandarac gum, dammars, elemis, copals; deoxyribonucleic acid, mucopolysaccharides such as hyaluronic acid, chondroitinsulphate, and mixtures thereof.

Silicas modified with hydrophobic groups such as trimethylsiloxyl groups, which are obtained in particular by treating pyrogenic silica in the presence of hexamethyldisilazane. Silicas thus treated are called "Silica silylate" according to the CTFA (6th edition, 1995). They are for example marketed under the references "AEROSIL R812®" by the company Degussa, "CAB-O-SIL TS-530®" by the company Cabot. Dimethylsilyloxyl or polydimethylsiloxane groups, which are in particular obtained by treating pyrogenic silica in the presence of polydimethylsiloxane or dimethyldichlorosilane. Silicas thus treated are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SIL TS-720®" by the company Cabot.

In one embodiment, the composition includes at least one polyol. Without being bound by theory, it is believed that the polyols supplement the exothermic action of the salts.

As polyols, there may be mentioned in particular the polyols having at least 2 hydroxyl groups and at least 3 carbon atoms, such as glycerine, diglycerine, and the glycols such as propylene glycol, dipropylene glycol, butylene glycol, hexylene glycol, polyethylene glycol, and polyethylene glycols having a molecular weight of less than 600, such as PEG-8 (or polyethylene 400), the sugars such as sorbitol, and mixtures thereof.

As polyols, glycerine, butylene glycol, propylene glycol, dipropylene glycol, PEG-8 and mixtures thereof are used in one embodiment.

The quantity of polyol(s) depends on the quantity of salts present in the composition and the heating effect desired. In one embodiment, the polyol is present from about 0.5% to about 80% by weight of the composition. In one embodiment, the polyol is present from about 5% to about 75% by weight of the composition. In one embodiment, the polyol is present from about 10% to about 70% by weight of the composition. In one embodiment, the polyol is present from about 30% to about 60% by weight of the composition.

In one embodiment, the composition includes cellulose beads. Representative cellulose beads include Cellulose Beads by DAITO KASEI KOGYO (Osaka, Japan). In one embodiment, the composition includes cellulose beads from about 0.05% to about 25% weight of the composition. In one embodiment, the composition includes cellulose beads from about 1% to about 10% weight of the composition. Cellulose beads are useful for absorbing oil and therefore controlling oil content in the composition.

In one specific embodiment, the composition includes at least one exothermic metal salt (as described above), at least one hydrophilic silica, and at least one hydrophobic silica, wherein the silicas act as gelling agents.

In a further embodiment, the exothermic metal salt is selected from magnesium sulfate, magnesium chloride, calcium chloride, calcium oxide, barium oxide, magnesium sulfate, ferric chloride, ferrous chloride, aluminum sulfate hexahydrate, and aluminum chloride.

In a further embodiment, the exothermic metal salt is magnesium sulfate.

In a further embodiment, the hydrophilic silica is a gelling agent.

In one embodiment, the hydrophobic silica is selected from silica silylate and silica dimethyl silylate. Such an embodiment is described in the EXAMPLES section below.

In one embodiment, the composition includes PEG 7 caprylic or capric glycerides, PEG-8, glycerin, citric acid, dimethicone or dimethiconol, silica dimethyl silylate, magnesium sulfate, and silica. Such an embodiment is described in the EXAMPLES section below.

In one embodiment, the composition includes PEG 7 caprylic or capric glycerides, PEG-8, glycerin, citric acid, dimethicone or dimethiconol, silica dimethyl silylate, magnesium sulfate, silica, capryloyl salicylic acid, kaolin, perlite, and talc. Such an embodiment is described in the EXAMPLES section below.

Mixing Energy

In one embodiment, the mixing energy is provided by a mechanical device. As disclosed herein, a mechanical (e.g. powered) brush is a representative mechanical device. Accordingly, in one embodiment, the cyclical mechanical motion is provided by a brush.

In one embodiment, the mechanical device is configured to provide a cyclical mechanical motion to produce the mechanical energy. In one embodiment, the cyclical mechanical motion is rotational or oscillating. Oscillating brushes, such as those of the Clarisonic® brand, are representative of the disclosed embodiments. In one embodiment, the cyclical mechanical motion has a peak cyclic or oscillation frequency of from about 40 Hz to about 240 Hz. In one embodiment, the cyclical mechanical motion has a peak cyclic or oscillation frequency of from about 158 Hz to about 178 Hz, which is the typical operating range of a Clarisonic® brand brush.

In one embodiment, the oscillation of the brush is at least 4 degrees, peak-to-peak, oscillation in the x-y plane (parallel to the user's skin). In another embodiment, the oscillation of the brush is at least 6 degrees, peak-to-peak, oscillation in the x-y plane. In another embodiment, the oscillation of the brush is at least 8 degrees, peak-to-peak, oscillation in the x-y plane.

Brush bristles can be constructed out of a variety of materials, such as polymers and co-polymers. In some embodiments, the bristles are constructed out of polybutylene terephthalate (PBT), such as DuPont™ Crastin®, polyethylene terephthalate (PET), such as DuPont™ Rynite®, nylons of differing blends, such as DuPont™ Zytrel®, polyester, such as DuPont™ Hytrel®, a thermoplastic elastomer (TPE), coextruded elastomers, polypropylene, polyethylene, such as DuPont™ Bynel®, combinations or blends thereof, such as DuPont™ SuperSoft®, etc. In some embodiments, the filaments may have cross sections including but not limited to circular, diamond, hollow, rectangular, X shape, multi-lobed, etc. The bristles may be treated with anti-microbial agents in some embodiments or coated or compounded with an anti-microbial material, such as silver zeolites, zinc, copper, etc., or other organic additives. End finishing of the bristles can also be selectively varied, some of which may be smooth polished end rounding, flat, tapered, raw cut, split, domed, semi-domed, etc. In some embodiments, one or more of the bristles may be flagged or multi-tipped.

Figure 3:
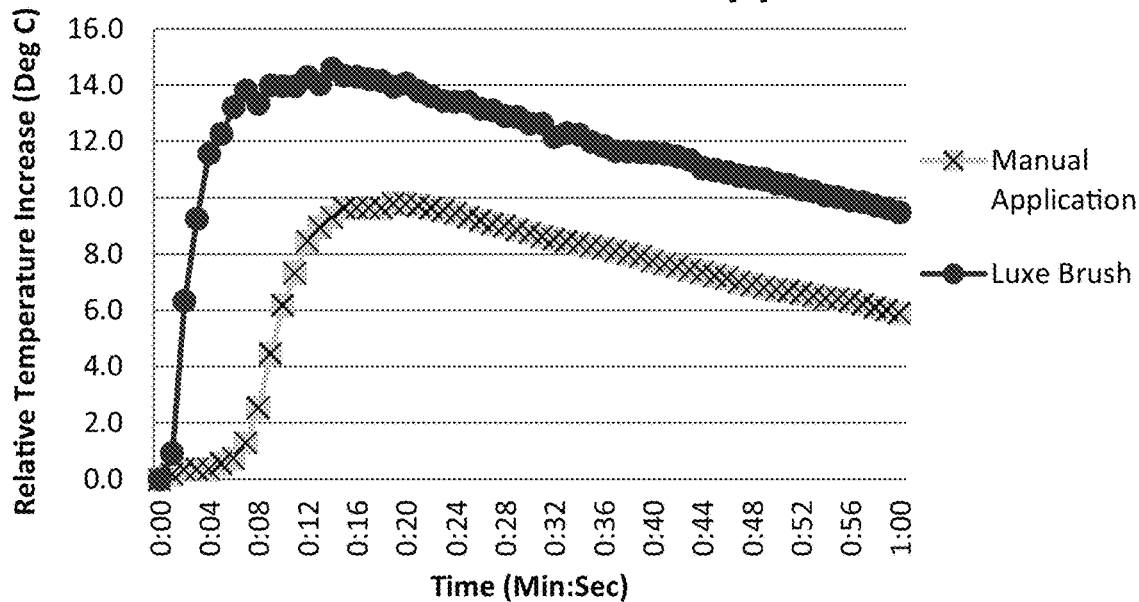
Figure 4:
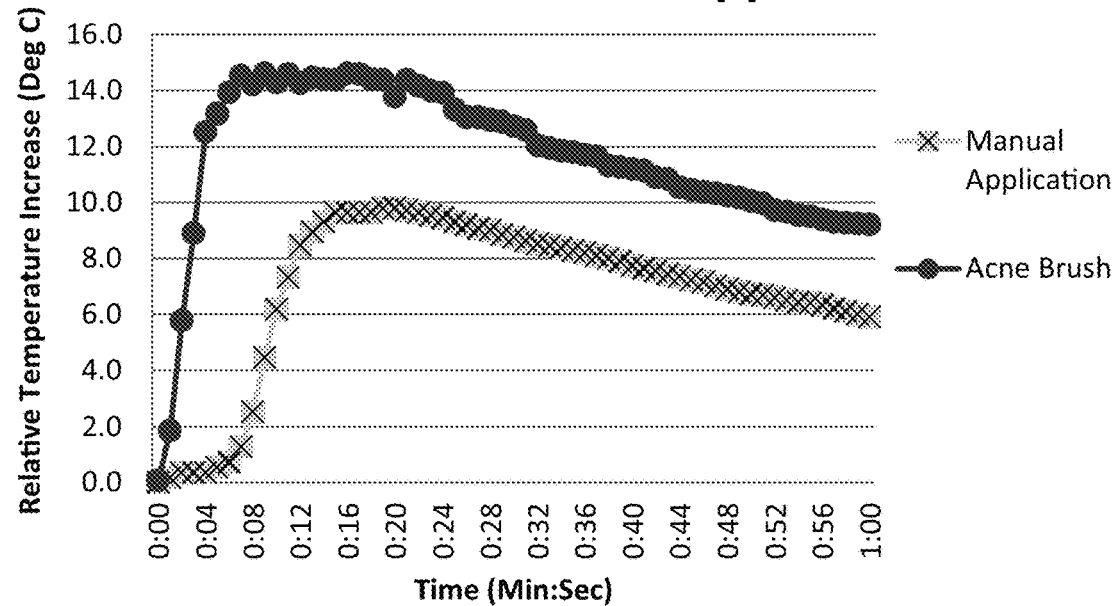
Figure 5:
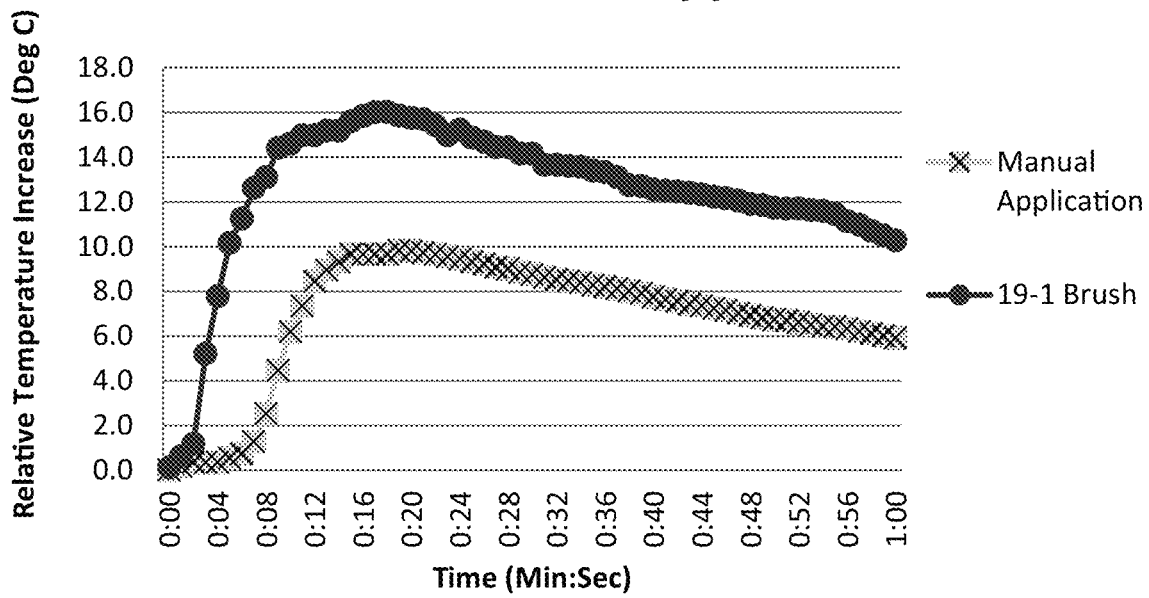
Figure 6:
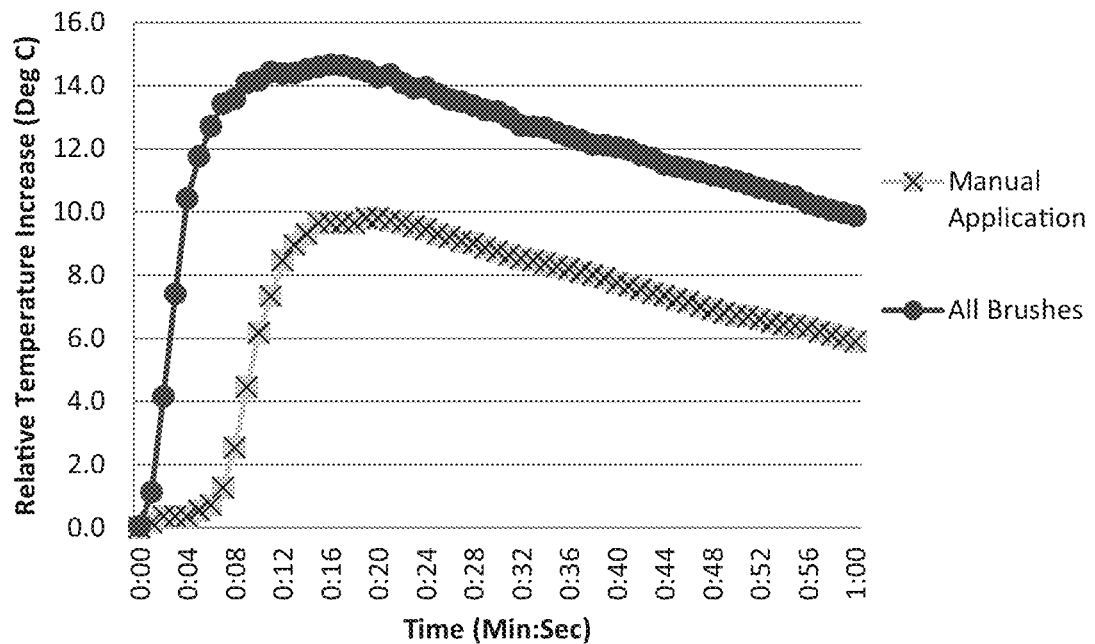
Figure 7:
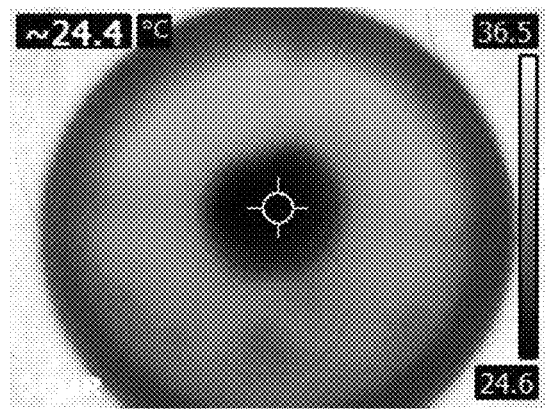
FIGS. 7 and 8 are thermal (infrared) images of a representative composition disposed on an exemplary brush before (FIG. 7) and after (FIG. 8) mechanical oscillation of the brush to mix the composition.
Figure 8:
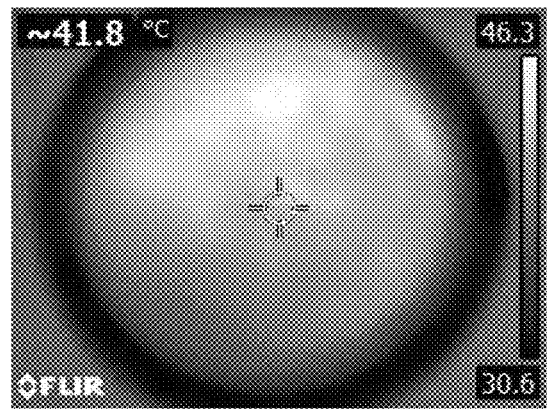
Figure 9:
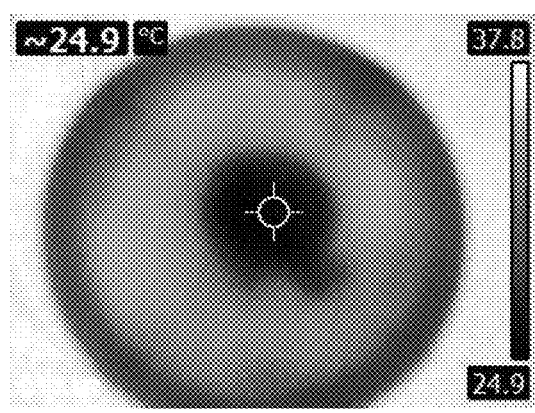
FIGS. 9 and 10 are thermal (infrared) images of a representative composition disposed on surface before (FIG. 9) and after (FIG. 10) manual mixing of the composition.
Figure 10:
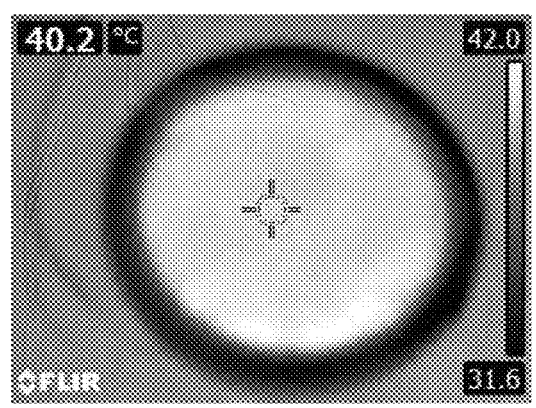
Figure 15:
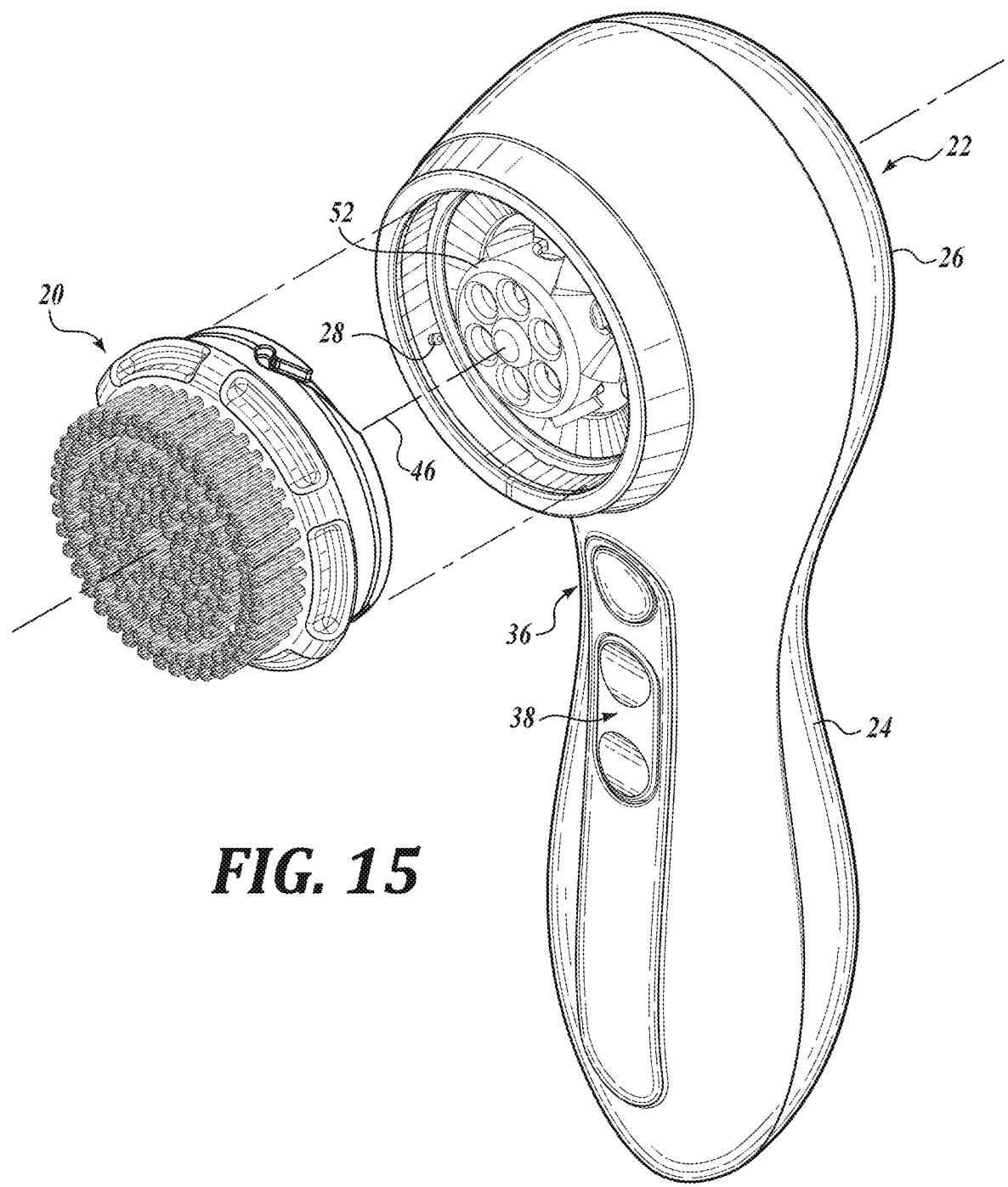
FIG. 15 is a perspective view of one example of a powered oscillating brush personal care appliance in accordance with embodiments disclosed herein.

Turning now to FIG. 15, there is shown one example of an appliance 22 in accordance with the disclosed embodiments having a workpiece configured to supply mixing energy to the composition. The appliance 22 includes a body 24 having a handle portion 26 and a workpiece attachment portion 28. The workpiece attachment portion 28 is configured to selectively attach a workpiece 20 (a brush, as illustrated) to the appliance 22. The appliance body 24 houses the operating structure of the appliance 22. An on/off button 36 is configured to selectively activate the appliance. In some embodiments, the appliance may also include power adjust or mode control buttons 38 coupled to control circuitry, such as a programmed microcontroller or processor, which is configured to control the frequency and amplitude of the oscillation of the workpiece 28. Brushes of the type illustrated in FIG. 3 are manufactured by Clarisonic®, including those brushes mentioned by product name herein. U.S. Pat. Nos. 7,786,626 and 7,157,816, both of which are hereby incorporated by reference in their entirety, are exemplary disclosures related to oscillating brushes useful in the disclosed embodiments.

Warming Effect

In one embodiment, the composition is configured to provide a minimum temperature increase by warming at least 10° C. upon exposure to water and mixing energy. In the exemplary compositions tested by the inventors, the use of mixing energy, in the form of an oscillating mechanical brush, increased the rise in temperature by up to 100%. For example, in one comparison, activating an exemplary composition according to Example 1 by hand yielded a temperature rise of 5-7° C. Using a Clarisonic® brush, the same composition generates a rise in temperature of 10-15° C. Any temperature increase due to kinetic energy produced by the brush is negligible (see FIG. 11).

So as to not harm the user, in one embodiment, the temperature rise does not produce a maximum temperature above 60° C.

In one embodiment, the composition is configured to warm for at least 60 seconds upon exposure to water and mixing energy. Such a timeframe is achieved in the Examples below and is necessary to convey long-lasting efficacy to a user. Additionally, activation of the composition by a brush results in a shorter duration before reaching peak warming when compared to activation by hand. Although the duration of the warming may last a similar amount of time, the user senses the heat quicker and more intensely when brush activation is used.

In one embodiment, the composition is configured to provide the minimum temperature increase for at least 60 seconds upon exposure to water and mixing energy. The minimum temperature increase, in one embodiment, is 8° C. In another embodiment, the minimum temperature increase is 10° C.

Figure 11:
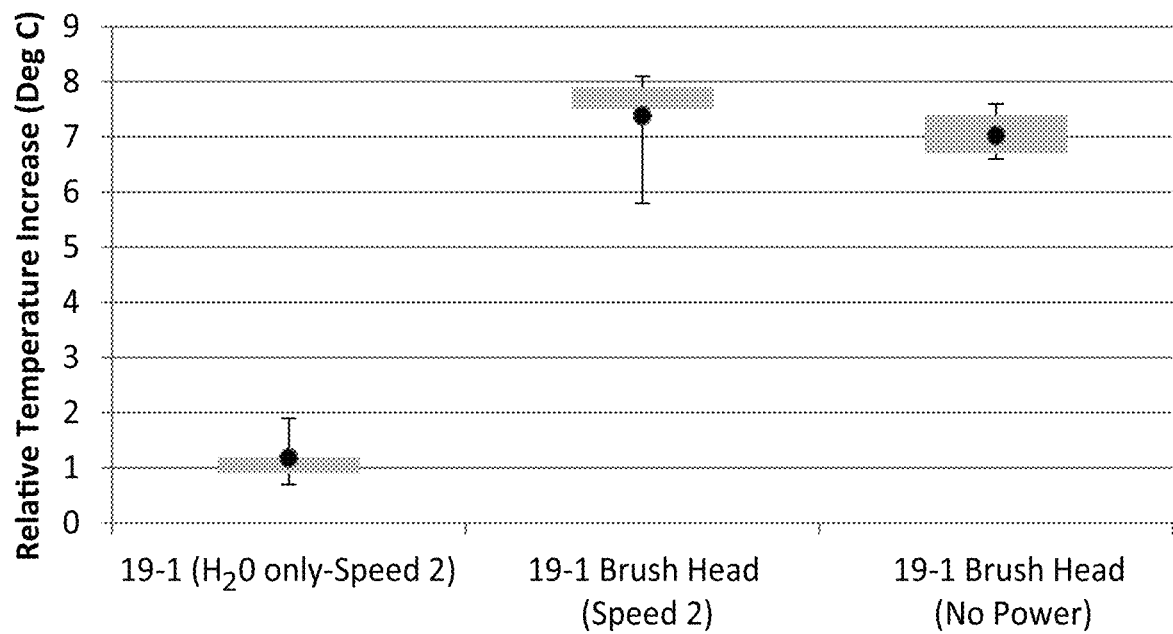
FIG. 11 graphically compares a representative composition used to increase temperature using a representative brush in various configurations.

In one embodiment, the composition is configured to produce an amount of warming energy that is greater than an amount of mechanical energy provided to the composition. In this regard, the composition provides heating that is greater than the heating that would be provided by the brush alone, as illustrated in FIG. 11. Furthermore, the composition produces greater heating when the brush is operated (e.g., oscillated; FIG. 11, center data) than if the brush is used to apply the composition without operation (FIG. 11, right-side data).

Kits Including the Composition and a Brush

In another aspect, a kit is provided that includes:
a composition that includes an anhydrous medium and at least one exothermic heating agent, wherein the composition is configured to provide increased temperature when exposed to water sufficient to initiate an exothermic reaction and mixing energy, as compared to the composition when exposed to water in the absence of mixing energy; and
a brush configured to
support the composition on a plurality of bristles of the brush;
deliver water to the composition in an amount sufficient to initiate the exothermic reaction of the exothermic heating agent; and
interface with a source of mechanical energy configured to provide sufficient movement of the brush to supply the mixing energy to the composition.

Compositions of the kit include any of the compositions disclosed herein. Brushes of the kit include any of the brushes disclosed herein. By pairing the composition and the brush together in a kit, an optimized system is provided to the consumer, wherein the composition and brush are tailored in characteristics in order to provide optimal performance of the composition when applied to a user's skin or hair by the brush (along with water to initiate the exothermic reaction of the exothermic heating agent).

Methods of Use

In another aspect, method of cleansing is provided, comprising applying mixing energy to a mixture of water and a composition as disclosed herein.

In some embodiments, the cosmetic composition is used for cleansing, such as cleansing skin or hair. The cosmetic composition is delivered to an area to be cleaned, such as a skin portion or a hair, water is applied, and sonic energy is applied to the mixture of water and the cosmetic composition. It is believed that sonic energy provides a more intense and longer lasting warming effect, when compared to manual application of the cosmetic composition. Without wishing to be bound by theory, it is believed that better cleansing can be achieved at higher temperatures, for example, as pores open and as make-up is more prone to dissolving.

In some embodiments, the mixture of water and the cosmetic composition is delivered to a skin portion or to hair. The sonic energy is applied to the mixture of water and the cosmetic composition after delivery of the mixture to the skin portion or to hair, to cleanse the skin portion or hair. In some embodiments, cleansing the skin portion includes exfoliating the skin portion. In certain embodiments, cleansing the skin portion includes removing make-up (when present) from the skin portion.

In one embodiment, the mixture of water and the composition is delivered to a skin portion or to hair.

In one embodiment, the mixing energy is applied to the mixture of water and the composition after delivery of the mixture to the skin portion or to hair, thereby cleansing the skin portion or hair.

In one embodiment, cleansing the skin portion further includes exfoliating the skin portion.

In one embodiment, cleansing the skin portion further includes removing make-up from the skin portion.

In one embodiment, the mixing energy is provided by a cyclic mechanical motion.

In one embodiment, the cyclic mechanical motion is rotational or oscillating.

In one embodiment, the cyclic mechanical motion is provided by a brush.

In one embodiment, the cyclic mechanical motion has a peak cyclic or oscillation frequency of from about 40 Hz to about 240 Hz.

In one embodiment, the composition warms by at least 10° C. upon exposure to water and mixing energy.

In one embodiment, the composition warms for at least 60 seconds upon exposure to water and mixing energy.

The following examples are included for the purpose of illustrating, not limiting, the disclosed embodiments.

EXAMPLES

Example 1. Comparison of Representative Composition Applied Manually and by Brush In this Example, a representative composition according to the disclosed embodiments, Composition 1, is evaluated based on Brushes Used Table 1, below, summarizes the different brush names used in the Examples.

TABLE 1

Brush types used in Examples.

| Brush Name | Filament Material | Filament Diameter (in) | Average Strand Count per Tuft | Trim/ Brush Height (in) |
|---|---|---|---|---|
| Sensitive | DuPont SuperSoft | 0.004 | 70-80 | 0.375 |
| Radiance | DuPont SuperSoft | 0.003 | 133-162 | 0.425 |
| Luxe Face | Tapered PBT | 0.003 | 133-162 | 0.8 |
| Acne | DuPont SuperSoft | 0.004 | 70-80/105-115* | 0.425 |
| 19-1 | Tapered PBT | 0.003 | 133-162 | 0.415 |

*The first number range refers to the outer 3 rings inner brush assembly on a Clarisonic brush head. The second number range refers to the inner 3 rings of the inner brush assembly.

Composition 1

Table 2 presents the amount by weight of each component of Composition 1.

TABLE 2

Composition 1 components.

| Component | Function | % by weight of composition |
|---|---|---|
| CITRIC ACID | Preservative, astringent, sequestering ingredient. | 1 |
| FRAGRANCE | Provides a pleasant scent to product. | 0.05 |
| PEG-8 | Colorless solvent, used as a humectant/skin conditioning agent, provides a modest heat effect. | 47.65 |

TABLE 2-continued

Composition 1 components.

| Component | Function | % by weight of composition |
|---|---|---|
| GLYCERIN | Solvent, humectant and emollient, assists in product spreadability | 5 |
| DIMETHICONE | A silicon oil, used as base ingredient and skin protectant. | 13.2 |
| SILICA DIMETHYL SILYLATE | Gelling agent/thickens oils. | 2 |
| DIMETHICONOL | A skin conditioning ingredient | 1.8 |
| MAGNESIUM SULFATE | Used as a thickener and an exothermic heating agent when merged with water. | 19.6 |
| SILICA | Gelling agent/thickener | 1 |
| WATER | Trace levels of water present with Magnesium Sulfate. | 0.4 |
| CAPRYLOYL SALICYLIC ACID | Keratolytic, Anti-inflammatory, Bactericide. | 0.3 |
| PEG-7 CAPRYLIC/ CAPRIC GLYCERIDES | Emollient | 8 |

Testing Methods
Equipment Used
1. Benchmark Hotplate—1 each
2. Thermometer—1 each
3. Control Company Thermometer (For Type K thermocouples)—1 each
4. Lab Companion Hotplate—1 each
5. Type K Thermocouples—3 each
6. Silicone Test Surface
   a. Custom Designed Geometry
   b. Material: Shore 40A Mold Max Silicone (created by 3D printed mold)
7. 1 Liter Glass Graduated Beaker (Generic)—1 each
8. 10 ML syringe (Generic)—1 each
9. Clarisonic® brush operated at Smart Profile Speed 2, 168 Hz providing an amplitude of 6-12 degrees.

Manual Application (Method V1)
1. Ensure the all materials are prepared—this should include the following
   a. "Water Temperature" is as indicated (i.e. 40 or 50) deg C. (+/−3 deg); record this in the trial log
   b. All 4 thermocouples are connected to the test surface, and ready to read a temperature. Temperature should be a minimum of 30 deg C.
   c. SD card is loaded into Thermometer
   d. Silicone Surface (or artificial skin) is clean and dry; no residual formula
2. Weigh out to grams of Composition 1 ("formula") in a weigh boat. A tolerance of +/−0.1 g is permissible, but should be noted in trial log
3. Apply formula to the Silicone Surface
4. Using a 10 ml syringe, pickup and discharge 10 ml of water, 3 times to heat the syringe
5. Apply water to the Silicone Surface using the syringe.
6. Note when the trial is started (for data logging reasons that are needed later)
7. Begin recording on the Thermocouple thermometer, ensuring that sampling is at a minimum 1 second/sample.
8. Start timer
9. Apply two fingers to surface to agitate the formula at a normal application force (~100-200 grams) for 1 minute. Move in a circular motion at ~2 rev/seconds. Use a Latex glove to keep a consistent application surface.
10. After applying fingers to surface for 1 minute, let rest and record data for an additional 1 minute at a minimum.
11. Stop recording data on the thermometer
12. Clean and dry silicone surface with a KimTech tissue Applicator Application Method (Method V1X)
1. Ensure the all materials are prepared—this should include the following
   a. "Water Temperature" is as indicated (i.e. 40 or 50) deg C. (+/−3 deg); record this in the trial log
   b. All 4 thermocouples are connected to the test surface, and ready to read a temperature. Temperature should be a minimum of 30 deg C.
   c. SD card is loaded into Thermometer
   d. Silicone Surface (or artificial skin) is clean and dry; no residual formula
2. Weigh out to grams of formula in a weigh boat. A tolerance of +/−0.1 g is permissible, but should be noted.
3. Apply formula to the Silicone Surface
4. Dip brush into the water for 5 seconds.
5. Shake once to remove excess water.
6. Begin recording on the Thermocouple thermometer, ensuring that sampling is at a minimum 1 second/sample.
7. Start timer
8. Turn on device to speed 2 to agitate the formula at a normal brushing force (~100-200 grams) of force for 1 minute. Move in a circular motion at ~2 rev/seconds.
9. After applying brush head to the surface for 1 minute, let rest and record data for an additional 1 minute, at a minimum.
10. Stop recording data on the thermometer
11. Clean and dry silicone surface with a KimTech tissue Data Processing
1. Open the raw data file in a spreadsheet format.
2. Create four new column headers (by data set) titled "Time", "TC1", "TC2", "TC3" and "TC4"
3. For each thermocouple, select the top cell and subtract the value that is in the cell, with the cell itself. This is "zeroing" out the temperature. Repeat for all 4 thermocouples
4. Select the 4 subtraction that were just created, and "ctl-d" to fill down the formula until the end of the data set
5. Find the point where the three cells start to show a temperature difference greater that 0 (or close to). Type in the cell above in the "Time" column "0:00".
6. The cell below that, type in 0:01 and the following cell 0:02.
7. Fill down the rest of the sequence until the end of the data set
8. Create a new column titled "Average".
9. Average the values for each of the thermocouples at each point in time.
10. Repeat step 9 until all values are average.
11. Highlight yellow and record maximum relative temperature for each thermocouple. Also note the time that this occurs. If the peak temperature occurs across a range of time, note the middle of this range.
12. Repeat steps 1-11 for as many data sets as necessary. Ensure that each data set is appropriately titled Results FIGS. 1-6 show the difference in temperature response for the Sensitive, Radiance, Luxe Face, Acne and 19-1 (Experimental) brushes vs manual application. In general the temperature difference when using a brush is 4-6 deg C. greater than that than manual application. No significant differences between brushes were detected.

FIGS. 7-10 show IR images of the two different application process (manual vs brush & device), each having a baseline and a peak temperature point. It should be noted the thermocouples showed a drop of ~2 deg when the brush peak image was taken, which was not shown with these images. This shows that the brush also acts a thermal insulator to ensure that heat is kept on the surface and not lost to the surrounding ambient conditions. The two probe points on both manual and brush application are random probe points. To get a sense of the real peak temperatures on the surface, refer to the thermal scale in each image and note the maximum temperature. This shows that the brush method has a peak temperature of ~4 degrees greater than the manual method of application.

FIG. 11 shows the different variables of the brush application method. In general, there is a temperature increase with water & formula, with or without oscillation from the device. This signifies that kinetic energy from the brush does not increase the heat significantly. However, when the brush is powered with warm water only (no formula added) the temperature increase is very small, signifying is the largest factor of a heat increase is when the water and the formula are mixed with the brush.

Figure 12:
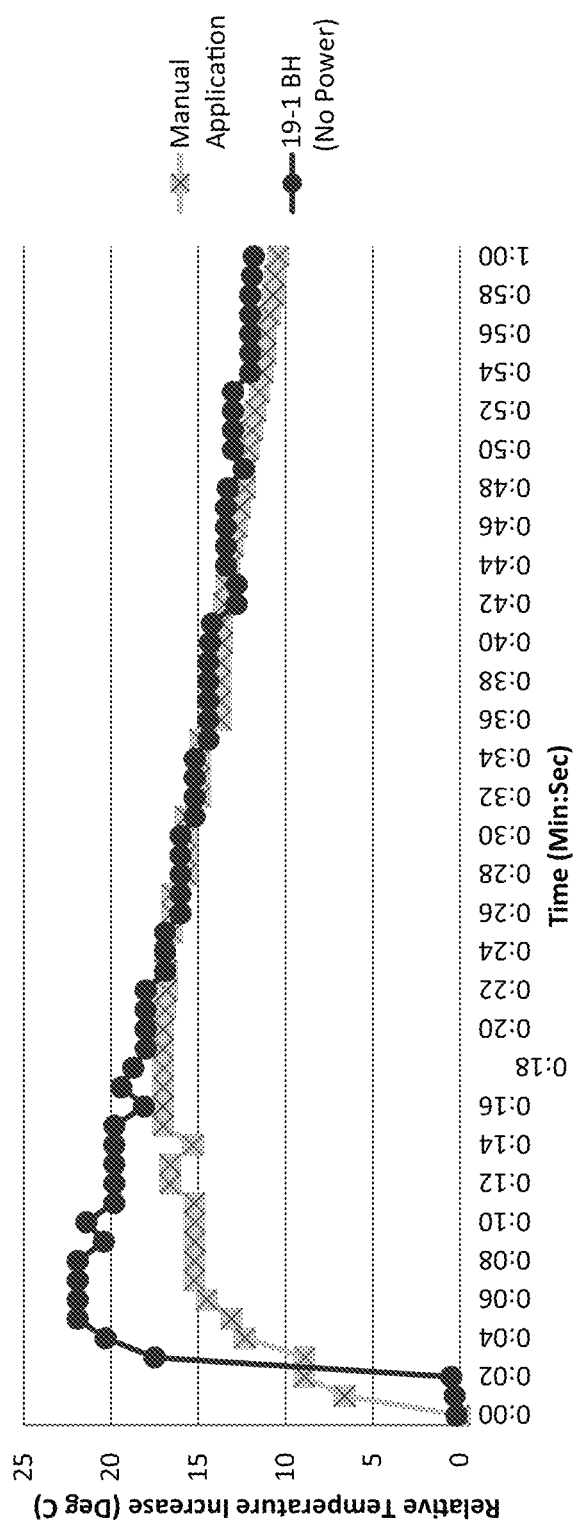
FIG. 12 graphically compares temperature increase versus time for a representative composition applied to an exemplary brush (with no brush movement) and manual application.
Figure 13:
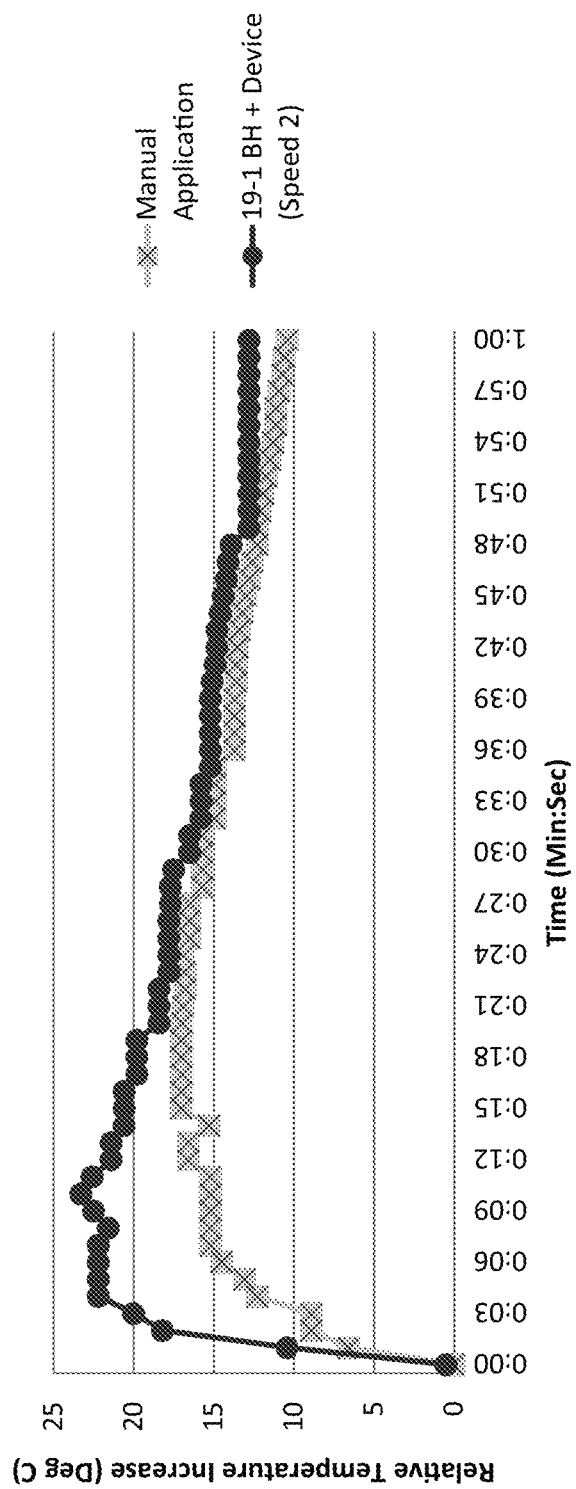
FIG. 13 graphically compares temperature increase versus time for a representative composition applied to an exemplary brush (with sonic oscillating brush movement) and manual application.

FIGS. 12-13 show that independent of power applied to the brush, the peak temperature is reached much faster when application occurs with a brush than manual application.

Figure 14:
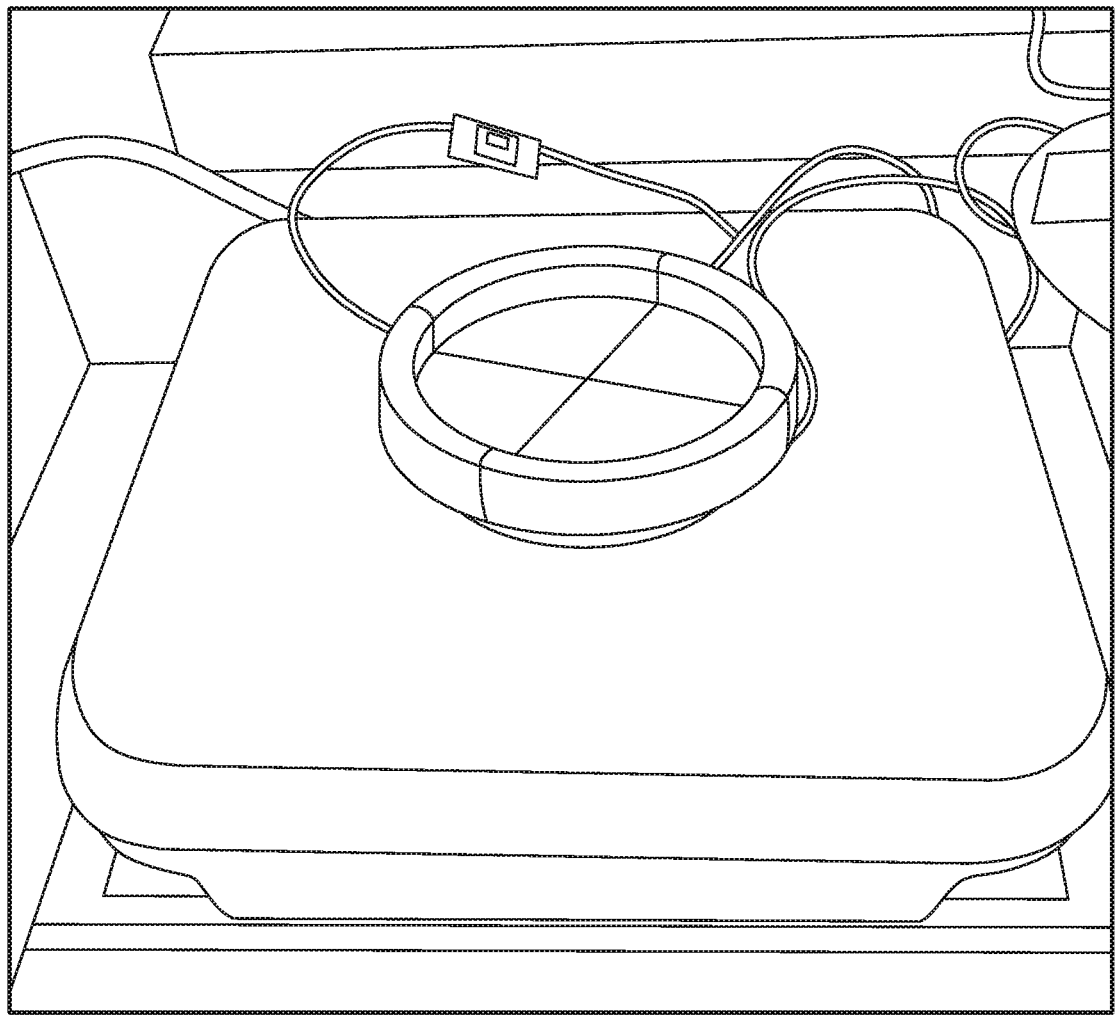
FIG. 14 is a photograph of an experimental testing apparatus used to measure the temperature of representative compositions applied either by brush or manually.

FIG. 14 is a photograph of the experimental testing apparatus used in this Example.

Conclusions

From the above data, in general a brush and a powered brush applied to Composition 1 will increase temperature further when compared to manual application. In between brushes, there is little difference between them regarding an increase in temperature. It can also be concluded the major factor of temperature increase is due to the brush's ability to create a harbor for a volume of water that reacts with the composition and not due to kinetic energy of the brush. The reaction time was also faster with a brush (independent of power) than compared to manual application. In general, the peak temperature was achieved from ~5-15 seconds with the brush and ~15-25 seconds with manual application.

Example 2: Comparison of Heating Provided by Representative Compositions

In this Example, a number of exemplary compositions are tested according to the methods described in Example 1. The compositions (see Table 3) include varying amounts of certain components in order to optimize the composition for use with a Clarisonic® Radiance brush (see Table 1 for brush characteristics).

TABLE 3

Exemplary compositions tested.

| Component | V 11 (%) | V 18 (%) | V 19 (%) | V 20 (%) | V 21 (%) |
|---|---|---|---|---|---|
| CAPRYLOYL SALICYLIC ACID | 0.3 | 0.3 | 0.3 | 0.3 | 0.3 |
| MAGNESIUM SULFATE (and) WATER | 20 | 10 | 5 | 20 | 20 |
| CITRIC ACID | 1 | 1 | 1 | 1 | 1 |
| SILICA | 1 | 1 | 1 | 1 | 1 |
| SILICA DIMETHYL SILYLATE | 2 | 2 | 2 | 2 | 2 |
| DIMETHICONE (and) DIMETHICONOL | 15 | 15 | 15 | 15 | 15 |
| PEG-8 | 47.7 | 57.7 | 62.7 | 54.7 | 50.7 |
| GLYCERIN | 5 | 5 | 5 | 5 | 5 |
| PEG-7 CAPRYLIC/CAPRIC GLYCERIDES | 8 | 8 | 8 | 1 | 5 |

Figure 16:
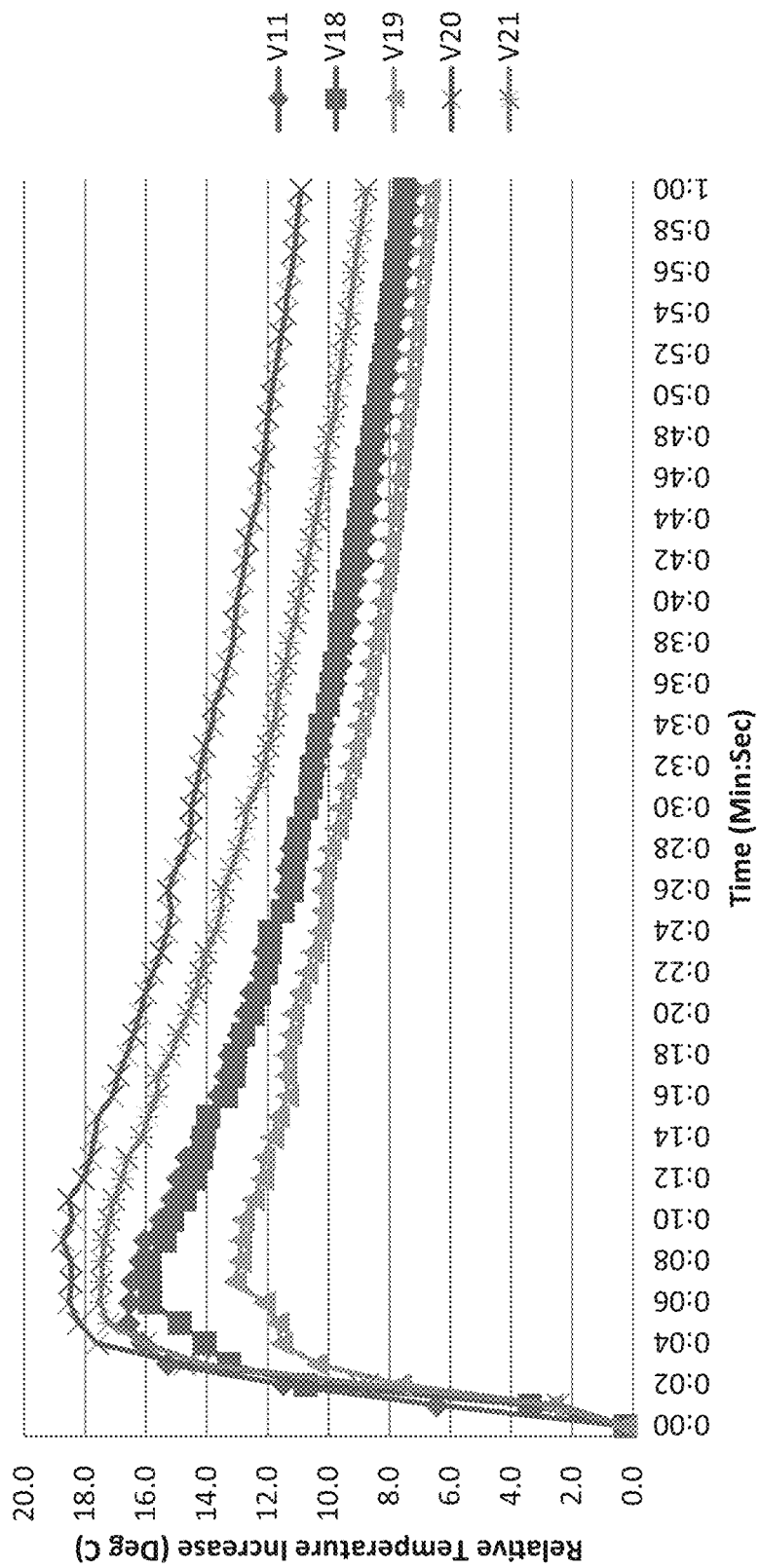
FIG. 16 graphically compares temperature increase versus time for a number of representative compositions applied to an exemplary brush (with sonic oscillating brush movement).

The results of the temperature monitoring are presented graphically in FIG. 16.

The level of magnesium sulfate has the greatest impact on the temperature results compared to other raw material/ingredients in the compositions. The higher the level of magnesium sulfate, the higher the average peak temperature and subsequent continued temperature. The results show that 5% and 10% magnesium sulfate provide lower average temperature increases versus the examples with 20% magnesium sulfate.

While keeping the magnesium sulfate levels the same, the level of PEG-8 has an impact on the temperature results, but not as pronounced as magnesium sulfate. V 20 has the higher level of magnesium sulfate with the higher level of PEG-8 and shows the highest peak temperature average. V 21 has the second highest PEG-8 ($MgSO_4$ is the same as V 20 and V 11) and has the second highest peak temperature average. V 11 has the third highest peak temperature average.

As used herein, the term "about" indicates that the subject number can be increased or decreased by 5% and still fall within the embodiment described or claimed.

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A composition, consisting of:
   19.6% by weight of magnesium sulfate,
   8% by weight of PEG-7 caprylic/capric glycerides,
   47.65% by weight of PEG-8,
   5% by weight of glycerin,
   1% by weight of citric acid,
   13.2% by weight of dimethicone,
   1.8% by weight of dimethiconol,
   2% by weight of silica dimethyl silylate,
   1% by weight of silica,
   0.05% by weight of fragrance,
   water, and
   0.3% by weight of capryloyl salicylic acid,
   wherein when the composition is exposed to water and subjected to cyclical mechanical mixing having a peak cyclic or oscillation frequency of 168 Hz, the composition provides a temperature increase of 4-6° C. greater than a temperature increase of the composition subjected to manual mixing.

2. The composition of claim 1, wherein the cyclical mechanical mixing is provided by a mechanical device.

3. The composition of claim 2, wherein the mechanical device is configured to provide a cyclical mechanical motion to produce the cyclical mechanical mixing.

4. The composition of claim 3, wherein the cyclical mechanical motion is rotational or oscillating.

5. The composition of claim 3, wherein the cyclical mechanical motion is provided by a brush.

6. The composition of claim 1, wherein the composition is configured to warm for at least 60 seconds upon exposure to water and cyclical mechanical mixing.

7. The composition of claim 1, wherein the composition is configured to produce an amount of warming energy that is greater than the amount of cyclical mechanical mixing provided to the composition.

8. A kit, comprising: the composition of claim 1; and a brush configured to provide a mechanical motion having a peak cyclic or oscillation frequency of from about 40 Hz to about 240 Hz.

9. A method of cleansing, comprising applying a mixture of the composition of claim 1 and water onto a skin portion or to hair; and applying cyclical mechanical mixing energy to the mixture to cleanse the skin portion or hair.

10. The method of claim 9, wherein cleansing the skin portion further includes exfoliating the skin portion.

11. The method of claim 9, wherein cleansing the skin portion further includes removing make-up from the skin portion.

12. The method of claim 9, wherein the cyclical mechanical mixing energy is provided by a cyclic mechanical motion.

13. The method of claim 12, wherein the cyclic mechanical motion is rotational or oscillating.

14. The method of claim 12, wherein the cyclic mechanical motion is provided by a brush.

15. The method of claim 12, wherein the cyclic mechanical motion has a peak cyclic or oscillation frequency of from about 40 Hz to about 240 Hz.

16. The method of claim 9, wherein the composition warms for at least 60 seconds upon exposure to water and cyclical mechanical mixing energy.

\* \* \* \* \*